Figure 1:
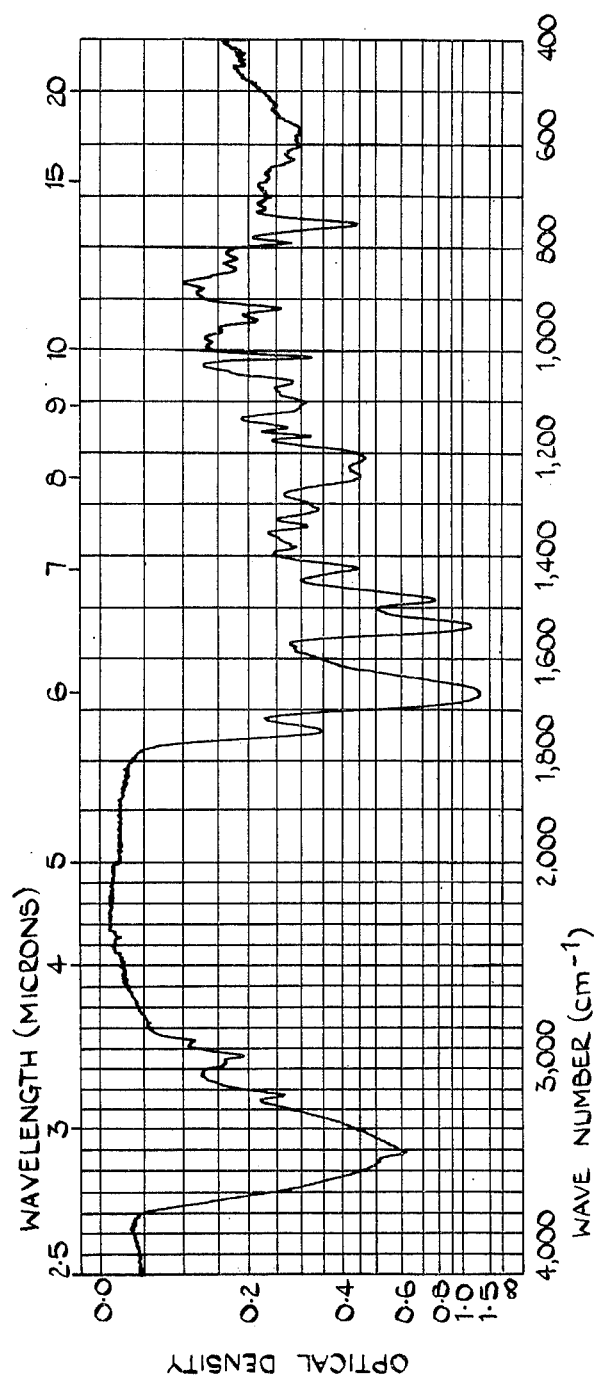

United States Patent [19]

Lombardi et al.

[11] 4,175,126
[45] Nov. 20, 1979

[54] POLYHETEROCYCLIC-ANTIBIOTIC

[75] Inventors: Bernard Lombardi, Soisy sur Seine; Jean Lunel, Paris, both of France

[73] Assignee: Rhone-Poulenc Industries, Paris, France

[21] Appl. No.: 930,148

[22] Filed: Aug. 2, 1978

[30] Foreign Application Priority Data

Aug. 4, 1977 [FR] France .................................. 77 24011

[51] Int. Cl.$^2$ ..................... A61K 31/44; C07D 515/22
[52] U.S. Cl. .................................... 424/263; 424/117; 260/239.3 P; 426/532
[58] Field of Search .................. 260/239.3 P; 424/263

[56] References Cited
PUBLICATIONS

Depaire et al. "Tetrahedron Letters" No. 16, pp. 1,395 to 1,406 (1977).

*Primary Examiner*—Alan L. Rotman
*Assistant Examiner*—Robert T. Bond
*Attorney, Agent, or Firm*—Stevens, Davis, Miller & Mosher

[57] ABSTRACT

The new antibiotic of the formula:

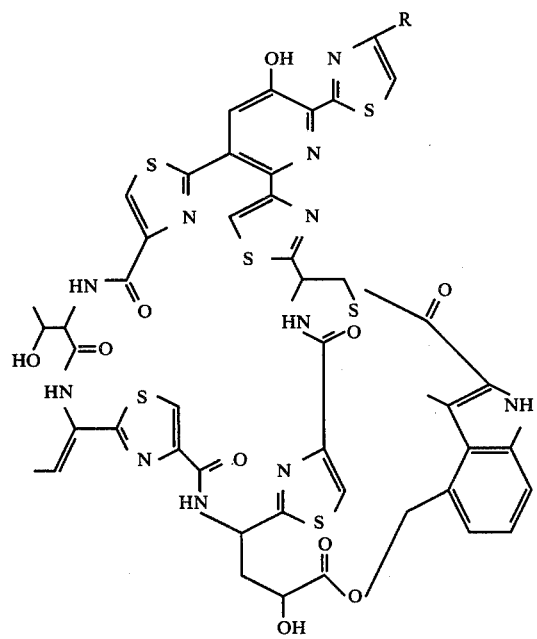

wherein R represents the group—$CONH_2$, designated 35665 RP, possesses growth-promoting properties when added to animal feed.

10 Claims, 3 Drawing Figures

POLYHETEROCYCLIC-ANTIBIOTIC

DESCRIPTION

The present invention relates to a new cyclopeptide antibiotic, hereinafter designated by the number 35665 RP, to a process for its preparation and compositions containing it.

The new antibiotic 35665 RP has a low toxicity and is particularly valuable as a growth factor which can be used in animal feeding.

The antibiotic 35665 RP, which has the empirical formula $C_{48}H_{40}O_{11}N_{12}S_6$, corresponds to formula I:

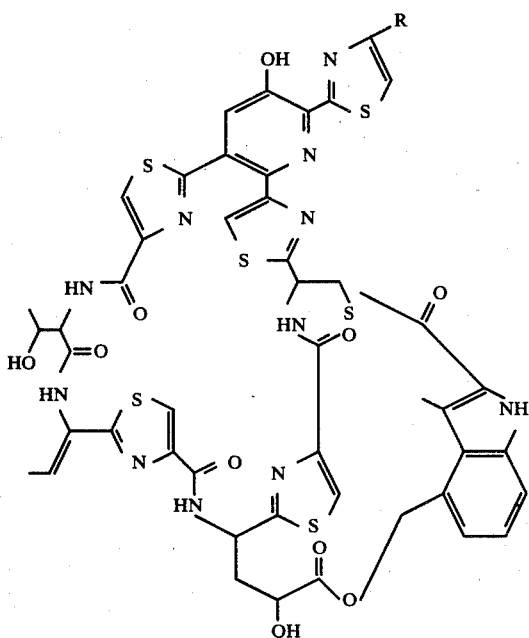

wherein R represents the group —$CONH_2$. 35665 RP has the following physico-chemical properties:

appearance: it is a yellowish amorphous powder;

solubility: it is soluble in dimethylformamide, pyridine and acetic acid and slightly soluble or insoluble in water, ethanol, acetone, chloroform and normal hexane;

melting point determination (in a capillary tube): it chars at 270° C. without melting up to 300° C.;

elementary analysis (on the compound as obtained):
% found C 48.3%, H 3.6%, O 16.6%, N 13.5%, S 15.35%:

calculated C 49.99%, H 3.50%, O 15.26%, N 14.57%, S 16.68%;

sulphate ash: 0.6%;

weight loss under reduced pressure at 100° C.: 5.9%;

35665 RP gives a negative ninhydrin test; after hydrolysis in 6 N hydrochloric acid for 20 hours under nitrogen at reflux, the product gives a positive ninhydrin test in accordance with its polypeptide nature;

ultra-violet spectrum (determination using a methanol solution containing 10.5 mg/liter):

$\lambda$ max=320 nm, $E_{1\ cm}^{1\%}$=313 (shoulder at about 295 nm);

visible spectrum (determination using a methanol solution containing 21 mg/liter):

$\lambda$ max=405 nm, $E_{1\ cm}^{1\%}$=107 (shoulder at about 372 nm);

infra-red spectrum (determination on tablets of a mixture with KBr): the principal infra-red absorption bands of 35665 RP, expressed in wave numbers ($cm^{-1}$), are given in Table I which follows:

TABLE I

| | | | |
|---|---|---|---|
| 3,450 ($H_2O$) | 1,538 vs | 1,168 m | 880 vw |
| 3,400 s | 1,510 sh. | 1,150 m | 845 m |
| 3,250 sh. | 1,485 s | 1,110 sh. | 825 m |
| 3,130 m | 1,422 m | 1,100 m | 790 m |
| 2,970 m | 1,382 m | 1,080 sh. | 755 s |
| 2,340 m | 1,370 sh. | 1,060 m | 725 vw |
| 2,860 w | 1,342 m | 1,040 sh. | 700 vw |
| 2,340 ($CO_2$) | 1,310 m | 1,012 m | 665 vw |
| 1,740 s | 1,300 sh. | 985 vw | 630 m |
| 1,665 vs | 1,245 m | 965 sh. | 600 w |
| 1,610 sh. | 1,210 m | 942 m | 570 w |
| 1,578 vw | 1,200 sh. | 918 m | 525 vw |
| | | | 650 to 400 ($H_2O$) | vs: very strong
m: medium
vw: very weak
s: strong
w: weak
sh.: shoulder

[this spectrum is shown in FIG. 1 in which the abscissae give the wavelengths expressed in microns (upper scale) and the wave numbers in $cm^{-1}$ (lower scale), and the ordinate gives optical densities];

rotatory power:

$[\alpha]_D^{20}=61\pm1.3°$ (c=0.88; pyridine).

Figure 2:
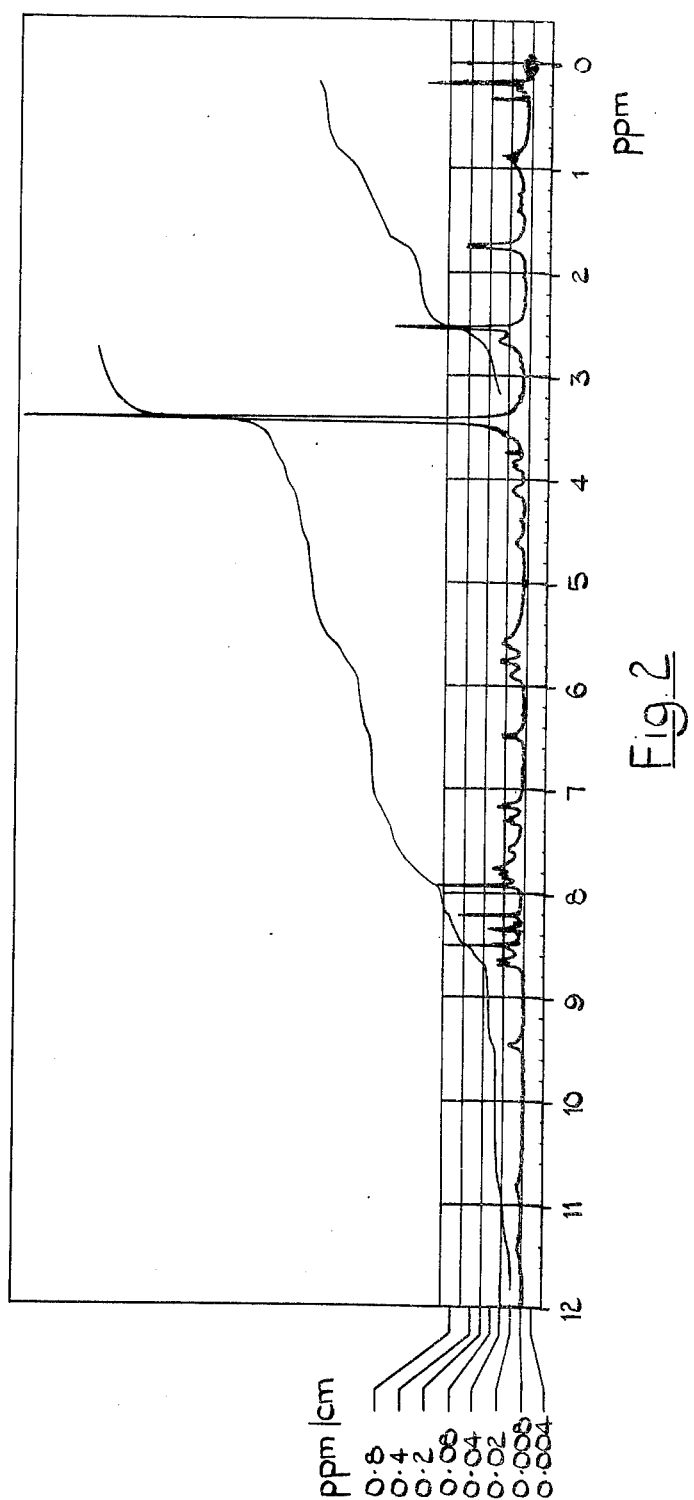

Further physico-chemical properties of 35665 RP are as follows:

Proton nuclear magnetic resonance spectrum in hexadeuterated dimethylsulphoxide: this spectrum, which is shown in FIG. 2, was recorded at a frequency of 250 MHz on a Cameca TSN 250 machine. The chemical shifts are given in Table 2 below. The chemical shifts $\delta$ are calculated positively in ppm towards low field from TMS (tetramethylsilane) taken as the internal reference. The coupling constants J are expressed in Hz.

TABLE 2

| Chemical shifts in ppm relative to TMS | Form of the signal; coupling constant J. |
|---|---|
| 0.86 | triplet |
| 0.8 to 1.2 | hump |
| 1.72 | doublet; (J = 7) |
| 2.3 to 2.8 | hump |
| 2.52 | multiplet |
| 3.42 | singlet |
| 3.84 | doublet of doublets; (J = 14 and 4) |
| 4.09 | multiplet |
| 4.36 | triplet; (J = 4.5) |
| 4.58 | multiplet |
| 5.3 to 5.7 | hump |
| 5.74 | doublet; (J = 6.5) |
| 5.88 | multiplet |
| 6.46 | quadruplet; (J = 6.5) |
| 7.13 | doublet; (J = 7) |
| 7.28 | triplet; (J = 7.5) |
| 7.56 | hump |
| 7.70 | shoulder |
| 7.62 to 7.89 | hump |
| 7.9 | singlet |
| 8.20 | singlet |
| 8.32 | singlet |
| 8.48 | singlet |
| 8.52 | shoulder |
| 8.62 | broad singlet |
| 8.67 | singlet |
| 9.44 | broad singlet |
| 10.80 | hump |
| 11.40 | hump |

Figure 3:
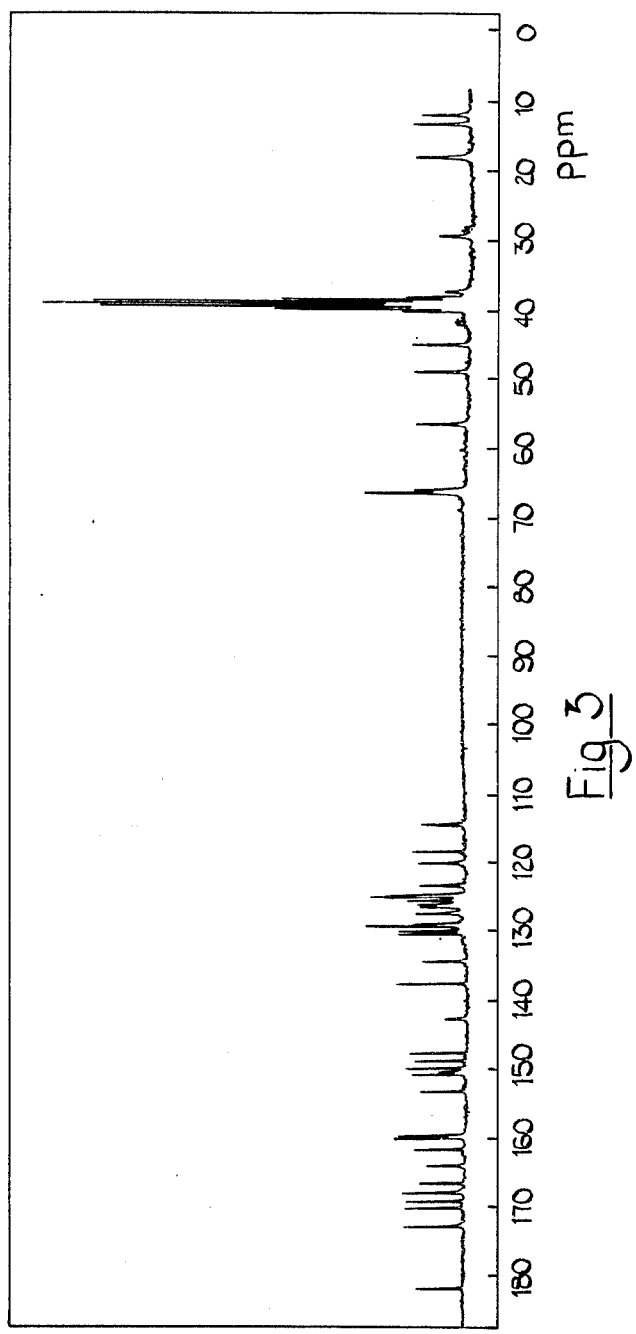

$^{13}$C nuclear magnetic resonance spectrum in hexadeuterated dimethylsulphoxide: this spectrum, which is shown in FIG. 3, was recorded at a frequency of 62.86 MHz on a Cameca TSN 250 machine. The chemical shifts are given in Table 3 below. The chemical shifts are measured in ppm, taking hexadeuterated dimethylsulphoxide as the internal reference at 39.5 ppm relative to TMS.

TABLE 3

| Chemical shifts in ppm relative to TMS | Form of the signal in the spectrum recorded "off-resonance" |
|---|---|
| 181.8 | singlet |
| 172.8 | singlet |
| 170.1 | singlet |
| 169.2 | singlet |
| 167.8 and 167.8 | singlet |
| 166.5 | singlet |
| 163.9 | singlet |
| 161.6 | singlet |
| 159.9 | singlet |
| 159.7 | singlet |
| 159.5 | singlet |
| 153.2 | singlet |
| 150.8 | singlet |
| 150.4 | singlet |
| 149.9 | singlet |
| 148.8 | singlet |
| 147.7 | singlet |
| 142.8 | singlet |
| 137.7 | singlet |
| 134.5 | singlet |
| 130.5 | singlet |
| 130.1 | singlet |
| 129.3 and 129.3 | singlet |
| 129.2 | doublet |
| 127.5 | doublet |
| 126.5 | doublet |
| 126.2 | doublet |
| 125.6 | doublet |
| 125.0 | singlet |
| 124.9 and 124.9 | doublet |
| 123.4 | doublet |
| 120.2 | doublet |
| 118.6 | singlet |
| 114.6 | doublet |
| 66.5 and 66.5 | doublet |
| 66.1 | triplet |
| 56.7 | doublet |
| 49.2 | doublet |
| 45.3 | doublet |
| 37.7 | triplet |
| 29.6 | triplet |
| 18.4 | quadruplet |
| 13.7 | quadruplet |
| 12.4 | quadruplet |

The proton and $^{13}$C nuclear magnetic resonance spectra show that 35665 RP contains 48 carbon atoms, of which 11 are sp$^3$ carbon atoms and 37 are sp$^2$ carbon atoms.

Thin layer chromatography: 35665 RP has an Rf of 0.16 in ascending chromatography on a thin layer of silica gel, using a benzene/methanol/acetic acid/pyridine mixture (75/10/2/15 by volume) as the developing solvent. The position of 35665 RP was observed using its yellow fluorescence under ultra-violet light at 366 nm.

Bacteriostatic activity: the bacteriostatic activity of 35665 RP towards a number of microorganisms was determined by a dilution method currently employed for this purpose. For each microorganism, the smallest concentration of substance which, under defined conditions, prevented any visible development in a suitable nutrient medium, was determined. The results of the various determinations are summarised in Table 4, in which the minimum bacteriostatic concentrations are expressed in micrograms of 35665 RP per cc of test medium.

TABLE 4

| Microorganism | Minimum inhibitory concentration (μg/cc) |
|---|---|
| Staphylococcus aureus - 209 P strain - ATCC 6538 P | 0.00051 |
| Staphylococcus aureus - 133 strain - Institut Pasteur | 0.0013 |
| Staphylococcus aureus - Smith strain | 0.0010 |
| Micrococcus lysodeikticus - ATCC 4698 | 0.00027 |
| Sarcina lutea - ATCC 9341 | 0.00046 |
| Streptococcus faecalis - ATCC 9790 | 0.0016 |
| Streptococcus faecalis - ATCC 8043 | 0.00078 |
| Streptococcus pyogenes - Dig 7 strain - Institut Pasteur | 0.00014 |
| Diplococcus pneumoniae - Til strain | 0.00017 |
| Neisseria catarrhalis - A 152 strain- Institut Pasteur | 0.0072 |
| Bacillus subtilis - ATCC 6633 | 0.0023 |
| Bacillus cereus - ATCC 6630 | 0.021 |
| Mycobacterium species - ATCC 607 | 50 |
| Escherichia coli - ATCC 9637 | greater than 200 |
| Proteus vulgaris - A 272 strain - Institut Pasteur | greater than 200 |
| Klebsiella pneumoniae - ATCC 10031 | greater than 200 |
| Pseudomonas aeruginosa - Bass strain- Institut Pasteur | greater than 200 |

The toxicity of 35665 RP was studied in mice. By oral administration 35665 RP is non-toxic at a dose of 2.5 g/kg animal body weight.

The antibiotic 35665 RP can be obtained by the careful hydrolysis of the antibiotic 9671 RP which is known as nosiheptide.

Nosiheptide and its preparation by the culture of Streptomyces actuosus (NRRL 2954) are described in British Patent Specification No. 945583. The structure proposed for this antibiotic has been published in Tetrahedron Letters, no. 16, pages 1,395 to 1,406 (1977) and it corresponds to formula I wherein R represents the grouping

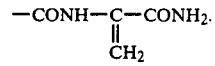

According to a feature of the present invention the antibiotic 35665 RP is prepared by the careful hydrolysis, under acidic conditions, of nosiheptide of the general formula I, wherein R represents a grouping of the formula

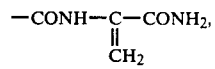

to convert that grouping to a group —CONH$_2$ without affecting the rest of the molecule. In particular the hydrolysis conditions should not cause rupturing of the peptide or lactone bonds.

The hydrolysis is preferably carried out by heating the nosiheptide in a solution of an inorganic acid in a neutral organic solvent or in an aqueous solution of an organic acid containing fewer than 3 carbon atoms, at a temperature of between 40° and 120° C. The reaction time is generally between 10 minutes and 4 hours, depending on the temperature and the acidity of the reaction medium. 1 to 5 N solutions of anhydrous hydrogen chloride in mixtures of methylene chloride and methanol, and 95% v/v aqueous acetic acid, may be mentioned as examples of a suitable reaction medium.

After precipitation by adding a poor solvent to the reaction mixture after hydrolysis, the 35665 RP obtained is separated from the reaction medium by filtration. The 35665 RP obtained can be purified by physicochemical methods such as chromatography.

The following Examples illustrate the preparation of 35665 RP.

EXAMPLE 1

A suspension of nosiheptide (100 mg) in an acetic acid/water mixture (90/10 by volume; 10 cc) is heated under reflux for 1 hour. After cooling, the solution obtained is poured into diethyl ether (100 cc). The precipitate which forms is filtered off, washed with diethyl ether (50 cc) and dried under reduced pressure (5 mm Hg) at 35° C.

The product thus obtained (100 mg) is purified, in two stages, by high performance liquid chromatography (HPLC) on a stainless steel column, having a length of 60 cm and a diameter of 0.75 cm, containing silica gel (about 15 g; particle size 10 to 40 $\mu$m, packed under a pressure of 300 bars). In each operation, a solution of the product (50 mg) in a chloroform/ethanol/water mixture (80/20/0.25 by volume; 1 cc) is injected into the column. The elution solvent consists of a chloroform/ethanol/water mixture (95/5/0.25 by volume).

Elution, which is carried out under a pressure of 50 bars (giving a flow rate of 2.5 cc per minute), is followed by continuous measurement of the optical density of the eluate at a wavelength of 360 nm.

The fraction containing 35665 RP is concentrated to dryness under reduced pressure in the absence of light. 35665 RP (13 mg) is thus obtained.

EXAMPLE 2

A suspension of nosiheptide (100 mg) in a mixture of methylene chloride and an 8 N solution of hydrogen chloride in methanol (70/30 by volume; 10 cc) is heated under reflux for 1 hour and the mixture is cooled to 20°-25° C.

The solution obtained is poured into diethyl ether (100 cc). The precipitate obtained is filtered off, washed with diethyl ether (50 cc) and dried under reduced pressure (5 mm Hg) at 35° C.

A product (100 mg) is thus obtained and is purified as described in Example 1. 35665 RP (27 mg) is thus obtained.

When added to animal feed, the antibiotic 35665 RP makes it possible to obtain a more rapid weight increase in the animal than with feeds in which it is absent. Furthermore, the antibiotic has the advantage that it is very stable to storage and that it can be mixed with all the usual products fed to animals, without fear of deterioration during storage.

The present invention includes within its scope animal feeds which comprise the antibiotic 35665 RP in association with animal feedstuff. Concentrated mixtures for animal feeding also constitute a feature of the invention.

The dose which is required in order to produce an appropriate effect can of course vary within fairly wide limits, depending on the animal species and the nutritive value of the feeds themselves. A content of 1 to 50 g of antibiotic 35665 RP per tonne of feed is generally sufficient in the rations fed to the animals.

The antibiotic 35665 RP can be present as a uniform dispersion in complete composite feeds at the above doses. It can also be distributed in supplementary feeds according to the invention which contain from 0.1 to 0.001% by weight of the antibiotic, in association with animal feedstuff, most frequently together with other additives such as vitamins and mineral salts. These supplementary feeds can either be mixed with the ration or consumed as they are and usually represent 5 to 20% of the ration.

Premixes according to the invention, which are used for the preparation of the complete rations or the supplementary feeds, usually contain from 0.05% to 20% by weight of antibiotic 35665 RP, in association with an edible extender. They constitute a convenient intermediate which facilitates the uniform distribution of the antibiotic 35665 RP in the feeds. The premixes themselves are generally obtained from concentrates which contain 99.9 to 20% by weight of antibiotic 35665 RP, in association with edible denaturants, such as edible dyestuffs, flavourings, dispersing agents or agents for preventing agglomeration, and edible extenders. A suitable concentrate can contain, e.g. 99% by weight of antibiotic 35665 RP with 0.1% by weight of dyestuff and 0.9% by weight of antiagglomerant.

The concentrates and premixes are generally pulverulent. The supplementary feeds and the complete composite feeds can either be pulverulent or in the form of granules prepared in accordance with the usual techniques. In these various compositions, the antibiotic 35665 RP can be in the form of fine particles which are free or covered with a coating.

The antibiotic 35665 RP can be suitably administered to all domestic animals and especially to poultry.

The following Example illustrates a composition according to the invention.

EXAMPLE 3

A feed for chicks, which has the following composition (% by weight), is prepared:

wheat flour—15%
maize flour—45%
fatty materials—0.8%
soya flour—25%
fish meal—7%
dried milk—1.2%
distillery solubles—2%
vitamin-enriched mineral complex—4%

The antibiotic 35665 RP is uniformly distributed in this feed at the rate of 5 g or 10 g per tonne of feed.

84 chicks (STUD 160 Whites, 42 cocks and 42 hens), are housed in batteries at the rate of 14 per compartment, using 6 compartments. The chicks are placed in hot batteries from the age of 1 day to 4 weeks and in cold batteries from the age of 4 weeks to 8 weeks. The feeds are supplied from day 1 and the cocks and hens are weighed at the age of 4 and 8 weeks.

The following are then determined:

(1) the weight gain of the chickens fed with the feed to which the antibiotic 35665 RP has been added at the doses indicated above, relative to that of chickens fed with a control feed not containing 35665 RP (expressed in %), and (2) the conversion index $$\left(\frac{\text{weight of feed consumed}}{\text{weight gain}}\right)$$

of the chickens fed with the feed to which the antibiotic 35665 RP has been added at the doses indicated above, relative to that of the chickens fed with the control feed (expressed in %).

The results are summarised in the following Table:

TABLE

| Product | Concentration in g/tonne | Weight gain (% relative to the controls) | |
|---|---|---|---|
| | | 0 to 4 weeks | 0 to 8 weeks |
| 35665 RP | 10 | 105 | 104.3 |
| 35665 RP | 5 | 103 | 107 |

| Product | Conversion index (% relative to the controls) | | Efficiency factor* | |
|---|---|---|---|---|
| | 0 to 4 weeks | 0 to 8 weeks | 0 to 4 weeks | 0 to 8 weeks |
| 35665 RP | 97 | 98.1 | 108.2 | 106.3 |
| 35665 RP | 99.3 | 98.1 | 103.7 | 109.1 |

*Efficiency factor = $\frac{\text{weight gained in \%} \times 100}{\text{conversion index in \%}}$

We claim:

1. A new antibiotic, herein designated 35665 RP, of the formula:

(I)

wherein R represents the group —$CONH_2$.

2. The antibiotic herein designated 35665 RP which has the following physico-chemical properties:

it is a yellowish amorphous powder which is soluble in dimethylformamide, pyridine and acetic acid and slightly soluble or insoluble in water, ethanol, acetone, chloroform and normal hexane;

in a melting point determination (in a capillary tube) it chars at 270° C. without melting up to 300° C.;

its elementary analysis is C 48.3%, H 3.6%, O 16.6%, N 13.5%, S 15.35%;

its sulphate ash is 0.6%;

its weight loss under reduced pressure at 100° C. is 5.9%;

it gives a negative ninhydrin test; after hydrolysis in 6 N hydrochloric acid for 20 hours under nitrogen at reflux, the product gives a positive ninhydrin test in accordance with its polypeptide nature;

its ultra-violet spectrum (determined using a methanol solution containing 10.5 mg/liter) shows an absorption maximum at 320 nm, $E_1\ _{cm}^{1\%}=313$ (with a shoulder at about 295 nm);

its visible spectrum (determined using a methanol solution containing 21 mg/liter) shows an absorption maximum at 405 nm, $E_1\ _{cm}^{1\%}=107$ (with a shoulder at about 372 nm);

its infra-red spectrum (determined on tablets of a mixture with KBr) shows characteristic absorption bands at 3,450 ($H_2O$), 3,400 (strong), 3,250 (shoulder), 3,130 (medium), 2,970 (medium), 2,940 (medium), 2,860 (weak), 2,340 ($CO_2$), 1,740 (strong), 1,665 (very strong), 1,610 (shoulder), 1,578 (very weak), 1,538 (very strong), 1,510 (shoulder), 1,485 (strong), 1,422 (medium), 1,382 (medium), 1,370 (shoulder), 1,342 (medium), 1,310 (medium), 1,300 (shoulder), 1,245 (medium), 1,210 (medium), 1,200 (shoulder), 1,168 (medium), 1,150 (medium), 1,110 (shoulder), 1,100 (medium), 1,080 (shoulder), 1,060 (medium), 1,040 (shoulder), 1,012 (medium), 985 (very weak), 965 (shoulder), 942 (medium), 918 (medium), 880 (very weak), 845 (medium), 825 (medium), 790 (medium), 755 (strong), 725 (very weak), 700 (very weak), 665 (very weak), 630 (medium), 600 (weak), 570 (weak), 525 (very weak) and 650 to 400 ($H_2O$); and its rotatory power, $[\alpha]_D^{20}$ is 61°±1.3° (c=0.88; pyridine).

3. Process for the preparation of the antibiotic herein designated 35665 RP which comprises the careful hydrolysis, under acidic conditions, of nosiheptide, of the formula depicted in claim 1, wherein the symbol R represents a grouping of the formula $$-CONH-\underset{CH_2}{\overset{\|}{C}}-CONH_2$$

to convert that grouping to a group —$CONH_2$ without affecting the rest of the molecule.

4. Process according to claim 3, in which the hydrolysis is carried out by heating the nosiheptide in a solution of an inorganic acid in a neutral organic solvent or in a aqueous solution of an organic acid containing fewer than 3 carbon atoms, at a temperature of between 40° and 120° C.

5. Process according to claim 4 in which the reaction time is between 10 minutes and 4 hours.

6. Process according to claim 3 in which the hydrolysis is carried out using a 1 to 5 N solution of anhydrous hydrogen chloride in a mixture of methylene chloride and methanol or using 95% v/v aqueous acetic acid.

7. An animal feed comprising 1 to 50 g of 35665 RP per tonne of feed.

8. A supplementary animal feed comprising 0.001 to 0.1% by weight of 35665 RP in association with animal feedstuff.

9. A premix comprising 0.05 to 20% by weight of 35665 RP in association with an edible extender.

10. A concentrate comprising 99.9 to 20% by weight of 35665 RP in association with an edible denaturant and extender.

* * * * *